US00PP34994P2

(12) United States Plant Patent
Van Swieten

(10) Patent No.: US PP34,994 P2
(45) Date of Patent: Feb. 21, 2023

(54) ***PHALAENOPSIS* ORCHID PLANT NAMED 'PHA202502'**

(50) Latin Name: ***Phalaenopsis* hybrid**
Varietal Denomination: PHA202502

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/803,422

(22) Filed: Jun. 29, 2022

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

CPVO hit of *Phalaenopsis* 'PHA202502' under UPOV, QZ PBR 2021/0302, published Jan. 29, 2021.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHA202502', particularly characterized by having purplish-red flowers with dark red-purple lips, flowers that are flat in lateral view, and flowers that have a bump and ridge on the upper and lower side of the apical lobes, is disclosed.

3 Drawing Sheets

Genus and species: *Phalaenopsis* hybrid.
Variety denomination: 'PHA202502'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA202502'.

The new *Phalaenopsis* plant is a product of a planned breeding program conducted by the inventor in Bleiswijk, the Netherlands. The objective of this breeding program was to create a new *Phalaenopsis* plant with numerous attractive purplish-red flowers with dark red-purple lips, suitable for potted plant production.

The new *Phalaenopsis* plant 'PHA202502' is a result of cross-pollination made by the inventor in September 2013 in Bleiswijk, the Netherlands, of the proprietary female, or seed parent, *Phalaenopsis* hybrid '41754-04' (unpatented), with a proprietary male, or pollen parent, *Phalaenopsis* hybrid 'PHALDUKAI' (U.S. Plant Pat. No. 28,157).

The new *Phalaenopsis* was selected by the inventor as a single plant within the progeny of the stated cross-pollination in a controlled greenhouse in Bleiswijk, the Netherlands, in July 2016. Asexual reproduction of the new *Phalaenopsis* plant by meristem tissue culture since 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Jan. 29, 2021

(Application No. 2021/0302), by Applicant who obtained the subject matter disclosed directly from the inventor. 'PHA202502' has not been made publicly available or sold anywhere in the world prior to the effective filing date of this application with the exception of sales or disclosures made one year or less before the effective filing date of this claimed invention by Applicant who obtained 'PHA202502' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA202502' as a new and distinct variety of *Phalaenopsis* plant:

1) Purplish-red flowers with dark red-purple lips;
2) Flower shape in lateral view is flat; and
3) Flower has a bump and ridge on the upper and lower side of the apical lobe.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in April 2022. Colors in the photographs may differ from the color values cited in the detailed botanical description, which accurately describe the actual colors of the new variety.

DESCRIPTION OF THE NEW VARIETY

Figure 1:
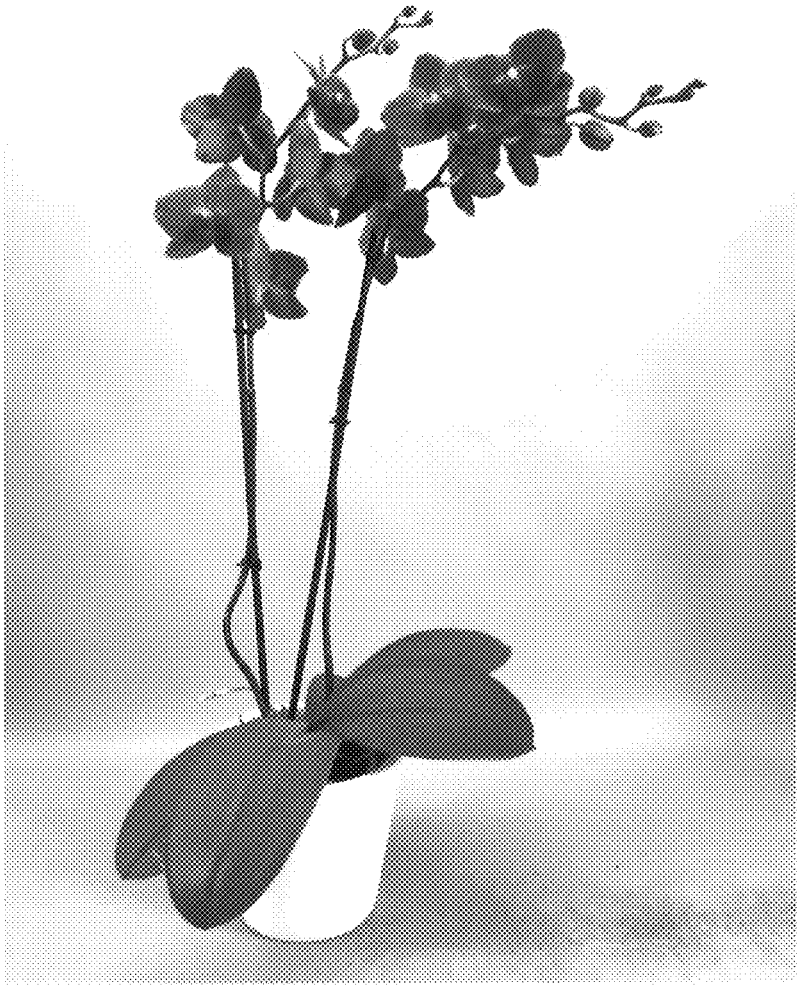
FIG. 1 shows the overall plant habit, including blooms, buds, and foliage of 'PHA202502'.
Figure 2:
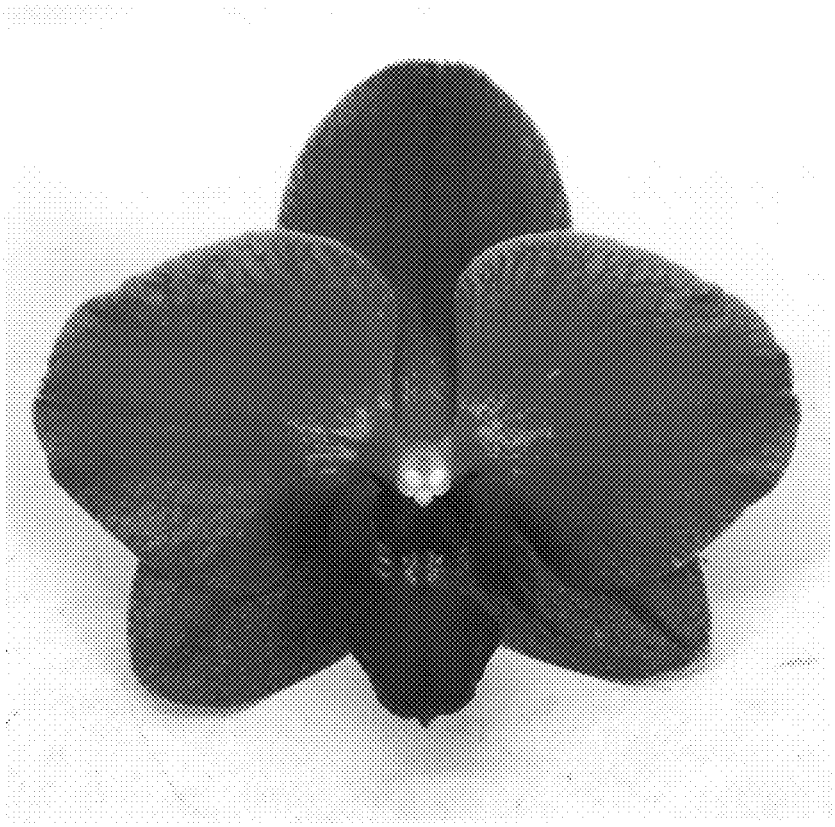
FIG. 2 shows a close-up of a flower of 'PHA202502'.
Figure 3:
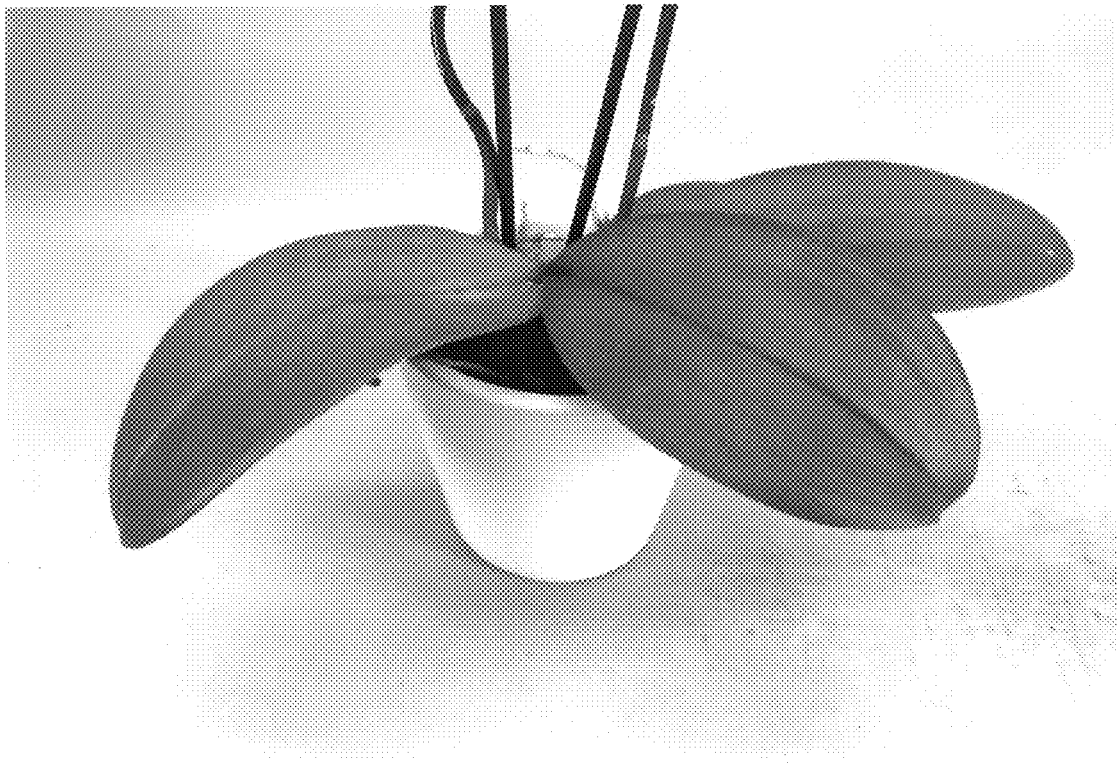
FIG. 3 shows an overhead view of the leaves of 'PHA202502'.

The following detailed description sets forth the distinctive characteristics of 'PHA202502'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in April 2022 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA202502'.

Parentage:

*Female parent*.—*Phalaenopsis* cultivar '41754-04' (unpatented).

*Male parent*.—*Phalaenopsis* cultivar 'PHALDUKAI' (U.S. Plant Pat. No. 28,157).

Propagation:

*Type*.—Meristem tissue culture.

Roots:

*Root description*.—Greyed-green (a color in between RHS 190B and RHS 190C) colored roots with branching lateral roots having light yellow-green (RHS 145B) with a touch of dark purplish-red (RHS N79B) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme inflorescence.

*Height* (*from soil level to top of inflorescence*).—Approximately 60.0 cm to 65.0 cm.

*Width* (*measured from leaf tips*).—About 36.0 cm to 38.0 cm.

*Vigor*.—Strong.

Leaves:

*Mature leaves*.—Quantity per plant: 7 to 8 leaves are produced before flowering. Length (fully expanded): 19.0 cm to 21.0 cm. Width: 9.0 cm to 10.0 cm. Position of the broadest part of the leaf: At the middle. Shape: Oblong. Base shape: Moderately elongated. Apex: Obtuse asymmetric. Leaf blade angle with the petiole (measured from the horizontal position): Between 5 degrees and 20 degrees. Leaf margin: Entire. Color: Upper surface: RHS 146A. Lower surface: RHS 146B with a dark red margin (RHS 187B). Texture (both upper and lower surfaces): Smooth. Thickness: 2.0 mm to 3.0 mm. Variegation: Absent. Venation: Pattern: Parallel. Color of the midvein: Upper surface: RHS 146A. Lower surface: RHS 146B with a hint of dark purplish-red (RHS N79B).

Peduncle:

*Quantity per plant*.—1 to 2.

*Number of flowers per peduncle*.—10 to 12.

*Length*.—60.0 cm to 65.0 cm.

*Diameter*.—4.0 mm to 5.0 mm.

*Strength*.—Strong.

*Aspect*.—Upright to slightly pendent.

*Texture*.—Smooth.

*Color*.—Mix of brown (RHS 200B) and yellow-green (RHS 146D).

*Internode length*.—5.0 cm to 6.0 cm.

Inflorescence description:

*Appearance*.—Upright to slightly pendent, raceme inflorescence with bilaterally symmetrical flowers that open in succession beginning with the lowermost flower.

*Number of inflorescences*.—1 to 2.

*Inflorescence size*.—Height (from base to tip): 270.0 mm to 310.0 mm.

*Flowering time*.—First flowers can be expected 10 to 11 months after planting in a 12-cm pot.

*Flower*.—Height: 73.0 mm to 78.0 mm. Diameter: 80.0 mm to 85.0 mm. Depth of lip: 23.0 mm to 25.0 mm.

*Flower shape*.—Flat.

*Flower longevity*.—On the plant: 16 to 18 weeks.

*Fragrance*.—Absent.

*Flower bud*.—Average size: Large. Length: 25.0 mm to 27.0 mm. Width: 20.0 mm to 22.0 mm. Shape: Egg shaped. Color: Touch of yellow-green (RHS 145B) at the base; dark purple-red (a color in between RHS N79C and RHS 187B).

*Petals*.—Arrangement: Open/free. Shape: Semi-circular. Apex: Rounded asymmetric. Margin: Moderately undulated. Length (from base to tip): 35.0 mm to 37.0 mm. Width: 42.0 mm to 44.0 mm. Position of the broadest part of the petal: Toward the base. Color (when fully opened): Upper surface: Basic color: Purplish-red (RHS 61A). Over color: Reddish-purple (RHS N78A) and light yellow dots (RHS 160D) at the base; dark red shade (RHS 59B) and purplish-red stripes (RHS 71A) toward the tip. Lower surface: Basic color: Purplish-red (RHS 186A). Over color: Touch of white (RHS 156D) at the base and reddish-purple (RHS 70B) from the base toward the middle. Number of spots, dots, and stripes on the petals (upper surface): Many very small dots and many stripes. Color of spots, dots, and stripes on the petals (upper surface): Dots (RHS 160D) and stripes (RHS 71A). Density of netting of the petals (upper surface): None. Color of the netting (upper surface): Not applicable.

*Dorsal sepal*.—Shape: Elliptic. Apex: Obtuse symmetric. Margin: Entire. Length (from base to tip): 40.0 mm to 42.0 mm. Width: 34.0 mm to 36.0 mm. Position of the broadest part of the dorsal sepals: At the middle. Color (when fully opened): Upper surface: Basic color: Purplish-red (RHS 61A). Over color: Touch of reddish-purple (RHS N78A) at the base; red shade (RHS 60A); purplish-red stripes and netting (RHS 71A); very small light yellow dots (RHS 160D). Lower surface: Basic color: Purplish-red (RHS 71A). Over color: Yellowish-green (RHS 195B) at the middle from the base toward the tip. Number of spots, dots, and stripes on the dorsal sepals (upper surface): Many dots and medium stripes. Color of spots, dots, and stripes on the dorsal sepals (upper surface): Dots (RHS 160D) and stripes (RHS 71A). Density of netting of the dorsal sepals (upper surface): Low. Color of the netting: RHS 71A.

*Lateral sepals*.—Shape: Ovate. Apex: Obtuse asymmetric. Margin: Entire. Length (from base to tip): 38.0 mm to 40.0 mm. Width: 29.0 mm to 31.0 mm. Position of the broadest part of the lateral sepals: Toward the base. Color (when fully opened): Upper surface: Basic color: Purplish-red (RHS 61A). Over color: Touch of reddish-purple (RHS N78A) at the base; dark red shade (RHS 187C); dark red stripes and netting (a color in between RHS 187B and RHS 187C) and light yellow dots (RHS 160B). Lower surface: Basic color: Purplish-red (RHS 186A). Over color: Light greenish-yellow shade and dots (RHS 160C); dark red (RHS 187C) midvein. Number of spots, dots, and stripes on the lateral sepals (upper surface): Many of very small dots and medium stripes. Color of spots, dots, and stripes on the lateral sepals (upper surface): Dots (RHS 160B) and stripes (a color in between RHS 187B and RHS 187C). Density of netting of the lateral sepals (upper surface): Low. Color of the netting (upper surface): A color in between RHS 187B and RHS 187C.

*Labellum* (*lip*).—Whiskers: Present. Length of whiskers: 5.0 mm to 7.0 mm. Color of whiskers: Dark red-purple (a color in between RHS 187B and RHS N79B); light greenish-yellow (RHS 8C) tips. Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Slightly undulated. Length: 14.0 mm to 16.0 mm. Width: 7.0 mm to 9.0 mm. Color: Upper surface: Touch of light yellow (RHS 160B) and white (RHS 155B) and striped (RHS 187C) at the base; dark red (RHS 187B) toward margin on one side and purplish-red (RHS 187D) toward tip and margin on the other side. Lower surface: White (RHS 155C) and red (RHS 179A) at the base; purplish-red (RHS 187D) and dark red (RHS 187B) toward one margin and the tip. Number of spots and stripes on the lateral lobe: Few stripes. Color of spots and stripes on the lateral lobe: RHS 187C. Density of netting of the lateral lobe: None. Color of the netting: None.

*Apical lobe*.—Shape: Trullate. Margin: Entire. Length: 19.0 mm to 21.0 mm. Width: 20.0 mm to 22.0 mm. Color: Upper surface: Touch of red (RHS 46A) at the base; dark red midvein and toward wings (RHS 187B); purplish-red (RHS 187D) toward the whiskers. Lower surface: Light yellow (RHS 160B) at the base; red (RHS 185A) at the middle; dark red wings (RHS 187B); reddish-purple (RHS N78A) toward whiskers. Number of spots and stripes on the apical lobe: None. Color of spots and stripes on the apical lobe: None. Density of netting of the apical lobe: None. Color of the netting: None. Bump and ridge (upper and lower surface): Present.

*Callus*.—Average size: Small. Height: 4.0 mm to 5.0 mm. Length: 4.0 mm to 5.0 mm. Width: 3.0 mm to 4.0 mm. Color: Yellow (RHS 13A) with dark reddish-orange stripes and dots (RHS 178B).

Reproductive organs:

*Column*.—Length: 8.0 mm to 9.0 mm. Diameter: 4.0 mm to 5.0 mm. Color: Purplish-pink (RHS N78C) with reddish-purple (RHS N78B) overcolor.

*Pollinia*.—Quantity: 2. Diameter: 0.8 mm to 1.0 mm. Color: Yellow-orange (RHS 23A).

*Ovary*.—Length: 10.0 mm to 12.0 mm. Diameter: 2.6 mm to 3.0 mm.

*Pedicel*.—Length: 33.0 mm to 35.0 mm. Diameter: 3.1 mm to 3.4 mm. Color: Yellow-green (RHS 146D) with a touch of dark purplish-red (RHS N79B) at the base; light yellow-green (RHS 76A) with a touch of light purple (RHS 76A) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA202502' differs from the female parent plant, cultivar '41754-04' (unpatented), in that 'PHA202502' has trullate apical lobes and weakly spatulated lateral lobes, whereas '41754-04' has rhombic apical lobes and ligulate lateral lobes. Additionally, 'PHA202502' has larger flowers than '41754-04' and the presence of whiskers.

The male parent plant of 'PHA202502', 'PHALDUKAI' (U.S. Plant Pat. No. 28,157), is no longer in existence, therefore a meaningful comparison cannot be made.

'PHA202502' is most similar to the commercial *Phalaenopsis* plants named 'PHALJAKYJE' (U.S. Plant Pat. No. 33,216) and 'PHA1904894' (U.S. Plant Pat. No. 33,554). 'PHA202502' differs from the commercial variety 'PHALJAKYJE' in that 'PHA202502' has obtuse dorsal sepal apexes, whereas 'PHALJAKYJE' has emarginated dorsal sepal apexes. Additionally, 'PHA202502' has the main color of the peduncle of brown, whereas 'PHALJAKYJE' has the main color of the peduncle of green with a touch of brown.

'PHA202502' differs from the commercial variety 'PHA1904894' in that 'PHA202502' has petals with moderate undulation of margin, whereas 'PHA1904894' has petals with weakly undulated margin. Additionally, 'PHA202502' has a longer internode length than 'PHA1904894'.

I claim:

1. A new and distinct variety of *Phalaenopsis* plant named 'PHA202502', substantially as described and illustrated herein.

* * * * *